(12) United States Patent
Sarver et al.

(10) Patent No.: US 10,765,510 B2
(45) Date of Patent: *Sep. 8, 2020

(54) HIGH DEFINITION AND EXTENDED DEPTH OF FIELD INTRAOCULAR LENS

(71) Applicant: Z Optics, Inc., Cookeville, TN (US)

(72) Inventors: Edwin J. Sarver, Cookeville, TN (US); James J. Simms, Medford, NJ (US)

(73) Assignee: Z Optics, Inc., Cookeville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/702,231

(22) Filed: Dec. 3, 2019

(65) Prior Publication Data

US 2020/0121450 A1    Apr. 23, 2020

Related U.S. Application Data

(63) Continuation of application No. 16/449,018, filed on Jun. 21, 2019, which is a continuation of application (Continued)

(51) Int. Cl.
*A61F 2/16*     (2006.01)
*A61F 9/008*   (2006.01)

(52) U.S. Cl.
CPC .......... *A61F 2/1637* (2013.01); *A61F 2/1618* (2013.01); *A61F 2/1654* (2013.01);
(Continued)

(58) Field of Classification Search
CPC .... A61F 2/1613; A61F 2/1637; A61F 2/1648; A61F 2/1656; A61F 2/1654
See application file for complete search history.

(56) References Cited

U.S. PATENT DOCUMENTS 4,976,732 A    12/1990   Vorosmarthy
5,121,980 A     6/1992   Cohen
(Continued)

FOREIGN PATENT DOCUMENTS

WO    WO-01/15635 A1     3/2001
WO    WO-2006/054178 A2  5/2006
(Continued)

OTHER PUBLICATIONS

Nishi, Y. et al. (2015). "Visual Simulation of Retinal Images with Various Designs of Pinhole Contact Lenses." *JSM Ophthalmol.* 3(1):1025 (5 pages).

(Continued)

*Primary Examiner* — William H Matthews
(74) *Attorney, Agent, or Firm* — Mintz Levin Cohn Ferris Glovsky and Popeo, P.C.

(57) ABSTRACT

A virtual aperture integrated into an intraocular lens is disclosed. Optical rays which intersect the virtual aperture are widely scattered across the retina causing the light to be virtually prevented from reaching detectable levels on the retina. The use of the virtual aperture helps remove monochromatic and chromatic aberrations yielding high-definition retinal images. For a given definition of acceptable vision, the depth of field is increased over a larger diameter optical zone. In addition, thinner intraocular lenses can be produced since the optical zone can have a smaller diameter. This in turn allows smaller corneal incisions and easier implantation surgery.

6 Claims, 10 Drawing Sheets

Related U.S. Application Data

No. 16/380,622, filed on Apr. 10, 2019, which is a continuation-in-part of application No. 14/686,233, filed on Apr. 14, 2015, now Pat. No. 10,285,807.

(52) U.S. Cl.
CPC ............ *A61F 2/1656* (2013.01); *A61F 9/008* (2013.01); *A61F 2002/169* (2015.04); *A61F 2009/0087* (2013.01)

(56) References Cited

U.S. PATENT DOCUMENTS

| | | |
|---|---|---|
| 5,628,794 A | 5/1997 | Lindstrom |
| 5,662,706 A | 9/1997 | Legerton et al. |
| 5,965,330 A | 10/1999 | Evans et al. |
| 5,980,040 A | 11/1999 | Xu et al. |
| 6,221,067 B1 | 4/2001 | Peyman |
| 6,874,886 B2 | 4/2005 | Miller et al. |
| 6,949,093 B1 | 9/2005 | Peyman |
| 7,287,852 B2 | 10/2007 | Fiala |
| 7,491,350 B2 | 2/2009 | Silvestrini |
| 7,628,810 B2 | 12/2009 | Christie et al. |
| 7,976,577 B2 | 7/2011 | Silvestrini |
| 8,079,706 B2 | 12/2011 | Silvestrini et al. |
| D656,526 S | 3/2012 | Christie et al. |
| 8,241,354 B2 | 8/2012 | Hong et al. |
| 8,287,592 B2 | 10/2012 | Silvestrini |
| 8,343,215 B2 | 1/2013 | Miller et al. |
| D681,086 S | 4/2013 | Christie et al. |
| 8,460,374 B2 | 6/2013 | Christie et al. |
| 8,740,978 B2 | 6/2014 | Weeber et al. |
| 8,752,958 B2 | 6/2014 | Miller et al. |
| 8,858,624 B2 | 10/2014 | Christie et al. |
| 8,864,824 B2 | 10/2014 | Silvestrini et al. |
| 9,005,281 B2 | 4/2015 | Christie et al. |
| 9,138,142 B2 | 9/2015 | Christie et al. |
| 9,204,962 B2 | 12/2015 | Silvestrini |
| 9,427,311 B2 | 8/2016 | Christie et al. |
| 9,427,922 B2 | 8/2016 | Reboul et al. |
| 9,492,272 B2 | 11/2016 | Christie et al. |
| 9,545,303 B2 | 1/2017 | Vilupuru et al. |
| 9,573,328 B2 | 2/2017 | Reboul et al. |
| 9,603,704 B2 | 3/2017 | Silvestrini |
| 9,844,919 B2 | 12/2017 | Reboul et al. |
| 9,848,979 B2 | 12/2017 | Vilupuru et al. |
| 9,943,403 B2 | 4/2018 | Webb et al. |
| 10,004,593 B2 | 6/2018 | Webb et al. |
| 10,183,453 B2 | 1/2019 | Reboul et al. |
| 2001/0050750 A1 | 12/2001 | Breger |
| 2003/0199976 A1 | 10/2003 | Portney |
| 2004/0230299 A1 | 11/2004 | Simpson et al. |
| 2005/0046794 A1 | 3/2005 | Silvestrini et al. |
| 2005/0125055 A1 | 6/2005 | Deacon et al. |
| 2006/0113054 A1 | 6/2006 | Silvestrini |
| 2006/0184243 A1 | 8/2006 | Yilmaz |
| 2006/0235428 A1 | 10/2006 | Silvestrini |
| 2006/0265058 A1 | 11/2006 | Silvestrini |
| 2006/0271184 A1 | 11/2006 | Silvestrini |
| 2009/0033863 A1 | 2/2009 | Blum et al. |
| 2009/0069817 A1 | 3/2009 | Peyman |
| 2009/0268155 A1 | 10/2009 | Weeber |
| 2009/0306773 A1 | 12/2009 | Silversrini et al. |
| 2011/0172675 A1 | 7/2011 | Danta et al. |
| 2012/0330415 A1 | 12/2012 | Callahan et al. |
| 2013/0053953 A1 | 2/2013 | Silvestrini |
| 2013/0238091 A1 | 9/2013 | Danta et al. |
| 2013/0289668 A1 | 10/2013 | Nirenberg et al. |
| 2014/0131905 A1 | 5/2014 | Webb |
| 2015/0025627 A1 | 1/2015 | Christie et al. |
| 2015/0366658 A1 | 12/2015 | Christie et al. |
| 2016/0157997 A1 | 6/2016 | Gerlach |
| 2016/0193037 A1 | 7/2016 | Pinto et al. |
| 2017/0143477 A1 | 5/2017 | Christie et al. |
| 2017/0156850 A1 | 6/2017 | Silvestrini |
| 2018/0125639 A1 | 5/2018 | Vilupuru et al. |
| 2018/0296322 A1 | 10/2018 | Webb et al. |
| 2018/0338826 A1 | 11/2018 | Link et al. |
| 2019/0076235 A1 | 3/2019 | Webb et al. |

FOREIGN PATENT DOCUMENTS

| | | |
|---|---|---|
| WO | WO-2008/137425 A2 | 11/2008 |
| WO | WO-2016/167906 A1 | 10/2016 |

OTHER PUBLICATIONS

Smith, George (1991). "Relation between Spherical Refractive Error and Visual Acuity" *Optometry Vis. Sci.* vol. 68, No. 8, pp. 591-598.

Yaish, S.B. et al. (2010). "Intraocular Omni-focal Lens With Increased Tolerance to Decentration and Astigmatism." *J Refract Surg.* 26(1):71-76.

HIGH DEFINITION AND EXTENDED DEPTH OF FIELD INTRAOCULAR LENS

CROSS REFERENCE TO RELATED APPLICATIONS

This Application is a Continuation of U.S. application Ser. No. 16/449,018 entitled "HIGH DEFINITION AND EXTENDED DEPTH OF FIELD INTRAOCULAR LENS" filed Jun. 21, 2019, which is a continuation of U.S. patent application Ser. No. 16/380,622 entitled "HIGH DEFINITION AND EXTENDED DEPTH OF FIELD INTRAOCULAR LENS" filed Apr. 10, 2019 which is a Continuation-in-Part of U.S. patent application Ser. No. 14/686,233 entitled "HIGH DEFINITION AND EXTENDED DEPTH OF FIELD INTRAOCULAR LENS" filed Apr. 14, 2015, now U.S. Pat. No. 10,285,807. The contents of the above referenced applications are incorporated herein by reference in its entirety.

BACKGROUND OF THE INVENTION

The human eye often suffers from aberrations such as defocus and astigmatism that must be corrected to provide acceptable vision to maintain a high quality of life. Correction of these defocus and astigmatism aberrations can be accomplished using a lens. The lens can be located at the spectacle plane, at the corneal plane (a contact lens or corneal implant), or within the eye as a phakic (crystalline lens intact) or aphakic (crystalline lens removed) intraocular lens (IOL).

In addition to the basic aberrations of defocus and astigmatism, the eye often has higher-order aberrations such as spherical aberration and other aberrations. Chromatic aberrations, aberrations due to varying focus with wavelength across the visible spectrum, are also present in the eye. These higher-order aberrations and chromatic aberrations negatively affect the quality of a person's vision. The negative effects of the higher-order and chromatic aberrations increase as the pupil size increases. Vision with these aberrations removed is often referred to as high definition (HD) vision.

Presbyopia is the condition where the eye loses its ability to focus on objects at different distances. Aphakic eyes have presbyopia. A standard monofocal IOL implanted in an aphakic eye will restore vision at a single focal distance. To provide good vision over a range of distances, a variety of options can be applied, among them, using a monofocal IOL combined with bi-focal or progressive addition spectacles. A monovision IOL system is another option to restore near and distance vision—one eye is set at a different focal length than the fellow eye, thus providing binocular summation of the two focal points and providing blended visions.

Monovision is currently the most common method of correcting presbyopia by using IOLs to correct the dominant eye for distance vision and the non-dominant eye for near vision in an attempt to achieve spectacle-free binocular vision from far to near. Additionally IOLs can be bifocal or multifocal. Most IOLs are designed to have one or more focal regions distributed within the addition range. However, using elements with a set of discrete foci is not the only possible strategy of design: the use of elements with extended depth of field (EDOF), that is, elements producing a continuous focal segment spanning the required addition, can also be considered. These methods are not entirely acceptable as stray light from the various focal regions degrade a person's vision.

What is needed in the art is an improved virtual aperture IOL to overcome these limitations.

SUMMARY OF THE INVENTION

Disclosed is a virtual aperture integrated into an intraocular lens (IOL). The construction and arrangement permit optical rays which intersect the virtual aperture and are widely scattered across the retina, causing the light to be virtually prevented from reaching detectable levels on the retina. The virtual aperture helps remove monochromatic and chromatic aberrations, yielding high-definition retinal images. For a given definition of acceptable vision, the depth of field is increased over a larger diameter optical zone IOL. Eyes with cataracts can have secondary issues due to injury, previous eye surgery, or eye disorder that would not be well corrected with normal IOL designs. Examples of eyes with complications include: asymmetric astigmatism, keratoconus, postoperative corneal transplant, asymmetric pupils, very high astigmatism, and the like. Because of its ability to remove unwanted aberrations, our virtual aperture IOL design would be very effective in provided enhanced vision compared to normal large optic IOLs.

An objective of the invention is to teach a method of making thinner IOLs since the optical zone can have a smaller diameter, which allows smaller corneal incisions and easier implantation surgery. Eyes with cataracts can have secondary issues due to injury, previous eye surgery, or eye disorder that would not be well corrected with normal IOL designs. Examples of eyes with complications include: asymmetric astigmatism, keratoconus, postoperative corneal transplant, asymmetric pupils, very high astigmatism, and the like. Because of its ability to remove unwanted aberrations, the disclosed virtual aperture IOL design is effective in providing enhanced vision compared to normal large optic IOLs.

Another objective of the invention is to teach a virtual aperture IOL that exhibits reduced monochromatic and chromatic aberrations, as well as an extended depth of field, while providing sufficient contrast for resolution of an image over a selected range of distances.

Still another objective of the invention is to teach a virtual aperture IOL that provides a smaller central thickness compared to other equal-powered IOLs.

Another objective of the invention is to teach a virtual aperture that can be realized as alternating high-power positive and negative lens profiles.

Yet still another objective of the invention is to teach a virtual aperture that can be realized as high-power negative lens surfaces.

Another objective of the invention is to teach a virtual aperture that can be realized as high-power negative lens surfaces in conjunction with alternating high-power positive and negative lens profiles.

Yet another objective of the invention is to teach a virtual aperture that can be realized as prism profiles in conjunction with alternating high-power positive and negative lens profiles.

Still another objective of the instant invention is to overcome these limitations by providing a phakic or aphakic IOL which simultaneously: provides correction of defocus and astigmatism, decreases higher-order and chromatic aberrations, and provides an extended depth of field to improve vision quality.

Another objective of the invention is to teach a virtual aperture that can be employed in phakic or aphakic IOLs, a corneal implant, a contact lens, or used in a cornea laser surgery (LASIK, PRK, etc.) procedure to provide an extended depth of field and/or to provide high-definition vision.

Yet another objective is to provide an IOL for eyes with complications such as asymmetric astigmatism, keratoconus, postoperative corneal transplant, asymmetric pupils, very high astigmatism, and the like.

Still another objective is to provide an IOL capable of removing unwanted aberrations to provide enhanced vision compared to normal large optic IOLs.

Another objective of the invention is to teach replacement of the virtual aperture with an actual opaque aperture and realize the same optical benefits as the virtual aperture.

Other objectives and further advantages and benefits associated with this invention will be apparent to those skilled in the art from the description, examples and claims which follow.

BRIEF DESCRIPTION OF THE DRAWINGS

FIG. 2 (A&B) illustrates the basic method of reducing chromatic aberrations using pupil size;

FIG. 3 (A&B) illustrates the basic concept of the virtual aperture to limit the effective pupil size;

FIG. 6 (A&B) illustrates the virtual aperture as a negative lens (or prism) section in conjunction to a high-power lens section;

FIG. 7 (A&B) illustrates using the virtual aperture to prevent the negative effect of a small optic zone;

DETAILED DESCRIPTION OF THE PREFERRED EMBODIMENT

Detailed embodiments of the instant invention are disclosed herein; however, it is to be understood that the disclosed embodiments are merely exemplary of the invention, which may be embodied in various forms. Therefore, specific functional and structural details disclosed herein are not to be interpreted as limiting, but merely as a basis for the claims and as a representation basis for teaching one skilled in the art to variously employ the present invention in virtually any appropriately detailed structure.

Figure 1:
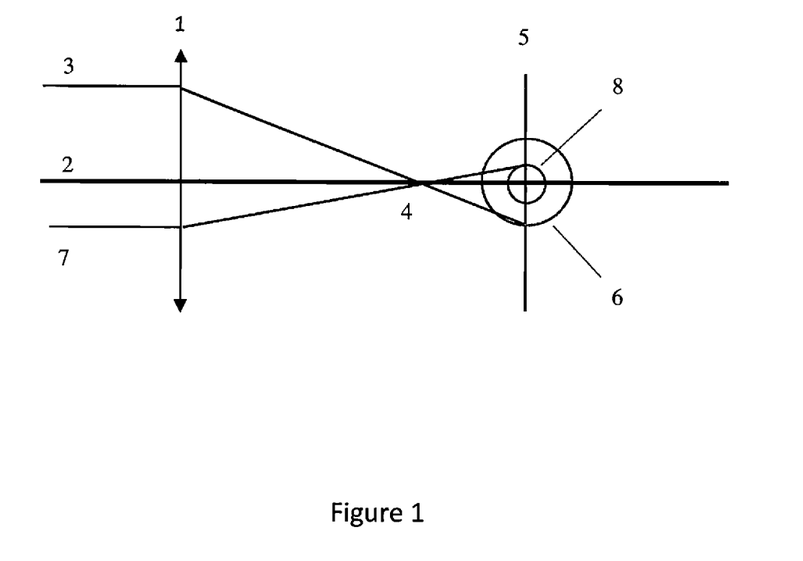
FIG. 1 illustrates the basic method of reducing monochromatic aberrations using pupil size.

FIG. 1 illustrates a single converging lens 1 centered on an optical axis 2. An incident ray 3 is parallel to the optical axis and will intersect the focal point 4 of the lens. If the observation plane 5 is located a further distance from the focal point, the incident ray will continue until it intersects the observation plane. If we trace all incident rays with the same ray height as incident ray 3, we will locate a blur circle 6 on the observation plane. Other incident rays with ray height less than incident ray 3 will fall inside this blur circle 6. One such ray is incident ray 7 which is closer to the optical axis than incident ray 3. Incident ray 7 also intersects the focal point 4 and then the observation plane 5. Tracing all incident rays with a ray height equal to incident ray 7 traces out blur circle 8 which is smaller than blur circle 6.

The optical principle represented here is that as the height of parallel incident rays is reduced, the corresponding blur circle is also reduced. This simple relationship is applicable to the human eye. Stated another way, for a given amount of defocus (dioptric error) in the eye, vision is improved as the height of incident rays is reduced. This principle is used when someone squints in an attempt to see an out-of-focus object more clearly.

Figure 2:
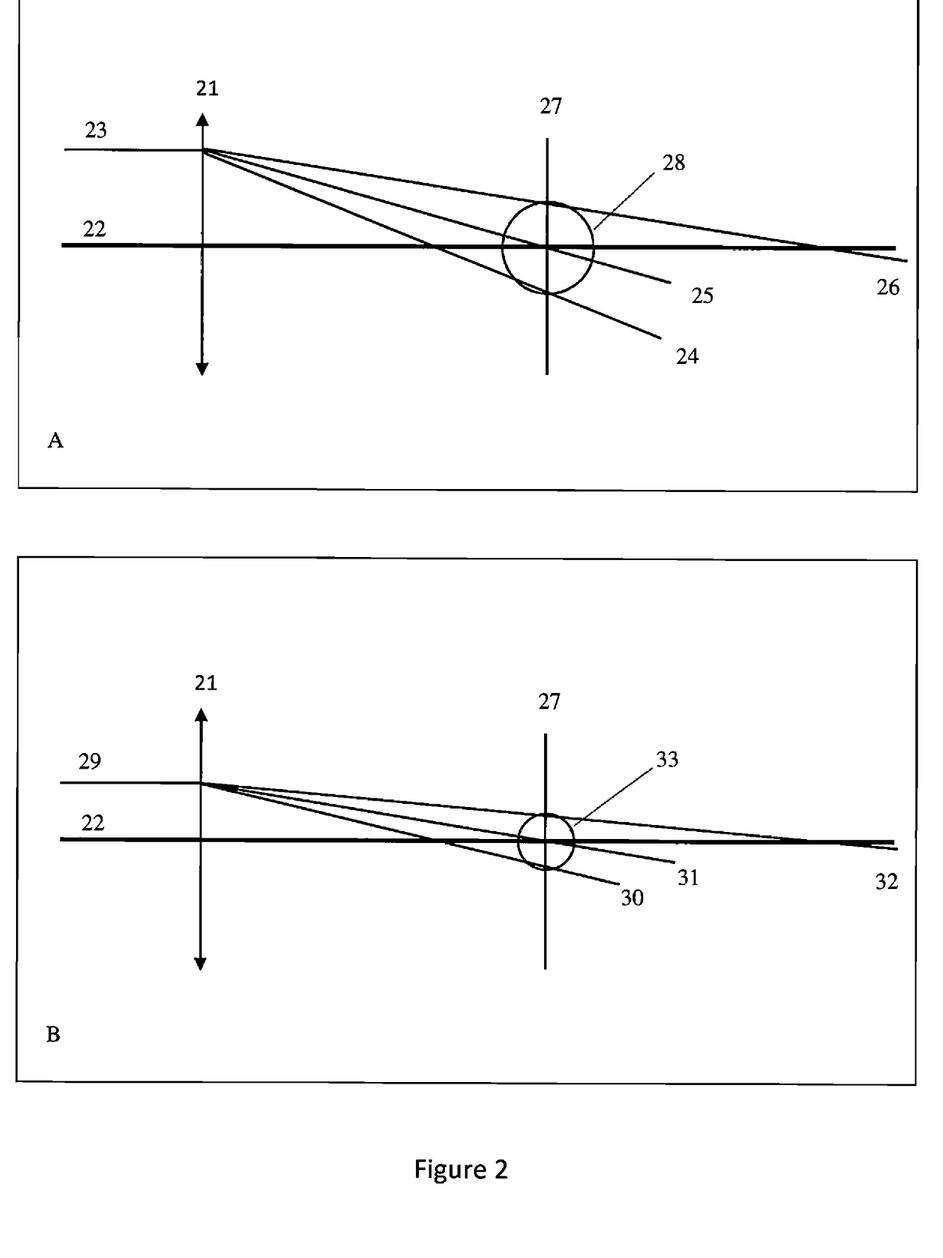

The tracing in FIG. 1 is for a single wavelength of incident light. For polychromatic light, three wavelengths in this case, we have the situation in FIG. 2. It is well known for the components of the eye and typical optical materials that, as wavelength increases, the refractive index decreases. In FIG. 2A, a converging lens 21 has optical axis 22. An incident ray 23 consists of three wavelengths for blue (450 nm), green (550 nm), and red (650 nm) light. Due to different indices of refraction for the three wavelengths, the blue light ray 24 is refracted more than the green light ray 25, and the green light ray is refracted more than the red light ray 26. If the green light ray is in focus, then it will cross the observation plane 27 at the optical axis. The chromatic spread of these three rays lead to a chromatic blur circle 28 on the observation plane. In FIG. 2B, the incident chromatic ray 29 has a lower ray height than the chromatic ray 23 in 2A. This leads to the smaller chromatic blur circle 33 at the observation plane. Thus, just as for the monochromatic of FIG. 1, chromatic blur is decreased as the chromatic ray height is decreased.

FIGS. 1 and 2 illustrate that decreasing ray height (decreasing the pupil diameter) decreases both monochromatic and chromatic aberrations at the retina, thus increasing the quality of vision. Another way to describe this is that the depth of field is increased as the ray height is decreased.

Figure 3:
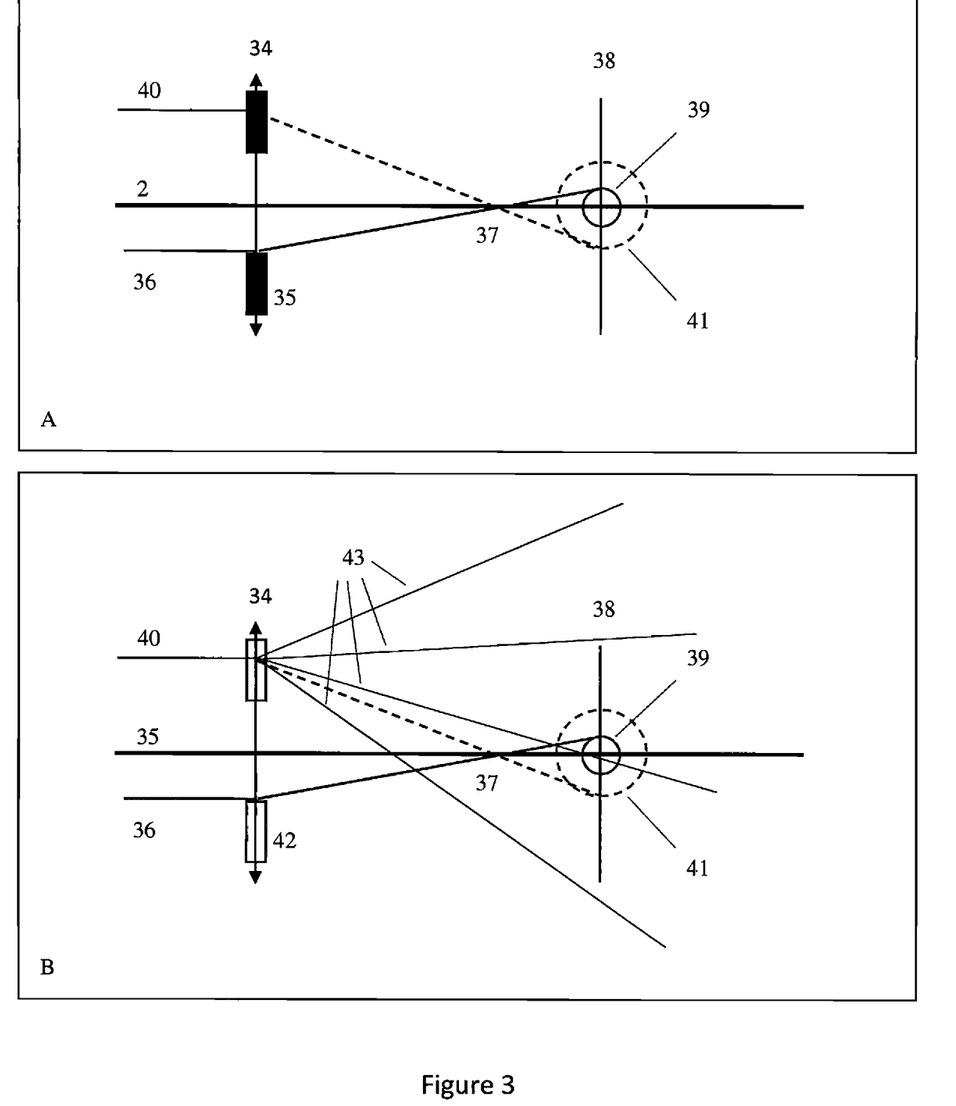

FIG. 3A illustrates a converging lens 34 with optical axis 2 and aperture 35. Incident ray 36 clears the aperture and thus passes through the lens focal point 37 and intersects the observation plane 38 where it traces a small blur circle 39. Incident ray 40 is blocked by the aperture, and thus it cannot continue to the observation plane to cause a larger blur circle 41. An aperture which limits the incident ray height reduces the blur on the observation plane. In FIG. 3B we illustrate what we describe as a "virtual aperture". That is, it is not really an aperture that blocks rays, but the optical effect is nearly the same. Rays 43 which propagate through the virtual aperture 42 are widely spread out so there is very little contribution to stray light (blurring light) at any one spot on the observation plane. This is the principal mechanism of operation of the IOL invention. Occasionally, a few months to a few years following cataract surgery and IOL implantation, a condition called posterior capsule opacification (PCO) develops over the clear posterior capsule and can interfere with quality vision. The incidence of PCO has been reported to be in the range of 5% to 50% of eyes undergoing cataract surgery and IOL implantation. Treatment to remove the PCO often involves intervention with a Nd:YAG laser to perform a posterior capsulotomy. In this case, the laser is focused through the IOL to perform the capsulotomy. If the virtual aperture were instead opaque, such as a true aperture, then this treatment would be inhibited. The disclosed virtual aperture is intentionally designed to provide the benefits of a small aperture while at the same time allowing a YAG capsulotomy to treat PCO.

Figure 4:
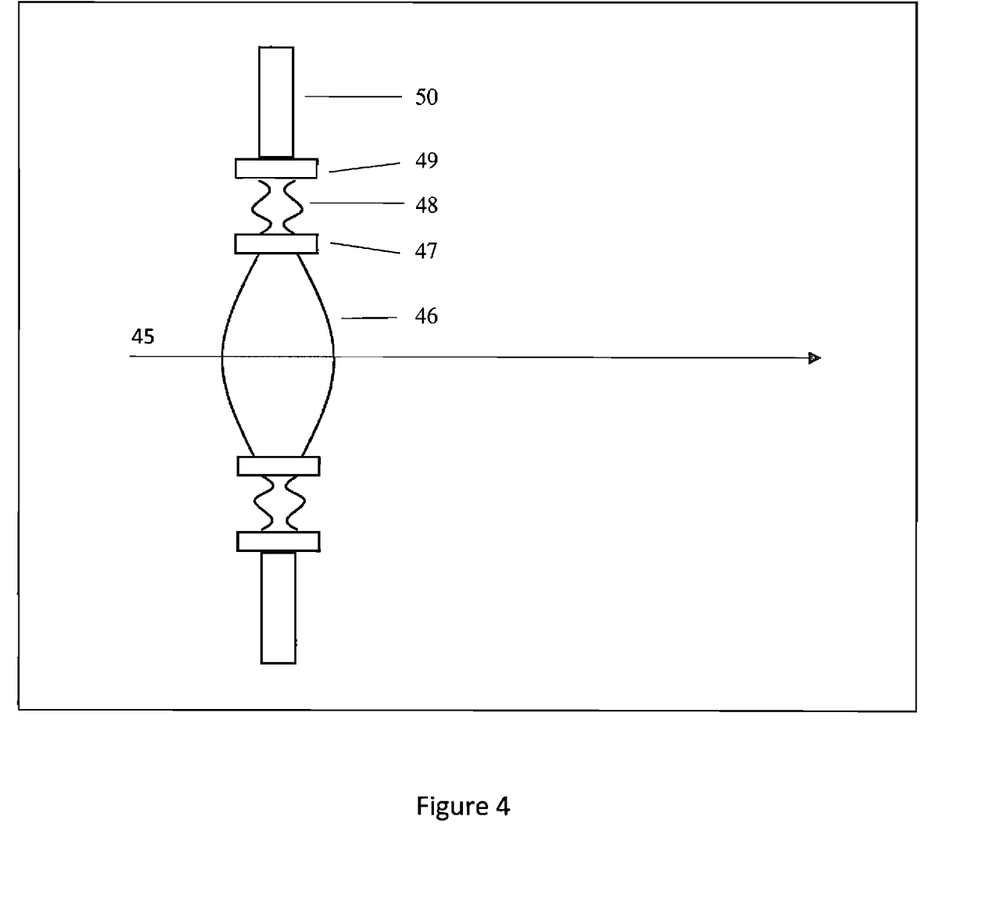
FIG. 4 illustrates the virtual aperture as a high-power lens section integrated into an IOL.

FIG. 4 illustrates a basic layout of an IOL which employs the virtual aperture. In this figure, a central optical zone 46 provides correction of defocus, astigmatism, and any other correction required of the lens. Generally, for an IOL using a virtual aperture, the central optical zone diameter is smaller than a traditional IOL. This leads to a smaller central thickness which makes the IOL easier to implant and allows a smaller corneal incision during surgery. The virtual aperture 48 is positioned further in the periphery and the IOL haptic 50 is located in the far periphery. The virtual aperture is connected to the optical zone by transition region 47 and the haptic is connected to the virtual aperture by transition region 49. The transition regions 47 and 49 are designed to ensure zero-order and first-order continuity of the surface on either side of the transition region. A common method to implement this is a polynomial function such as a cubic Bezier function. Transition methods such as these are known to those skilled in the art.

In the preferred embodiment, the virtual aperture zone 48 is a sequence of high-power positive and negative lens profiles. Thus, light rays which intersect this region are dispersed widely downstream from the IOL. These profiles could be realized as sequential conics, polynomials (such as Bezier functions), rational splines, diffractive profiles, or other similar profiles, as long as the entire region properly redirects and/or disperses the refracted rays. The preferred use is smooth high-power profiles over diffractive profiles as this simplifies manufacturing the IOL on a high-precision lathe or with molds. As known to those skilled in the art, the posterior side of the haptic should include a square edge to inhibit cell growth leading to posterior capsule opacification.

Figure 5:
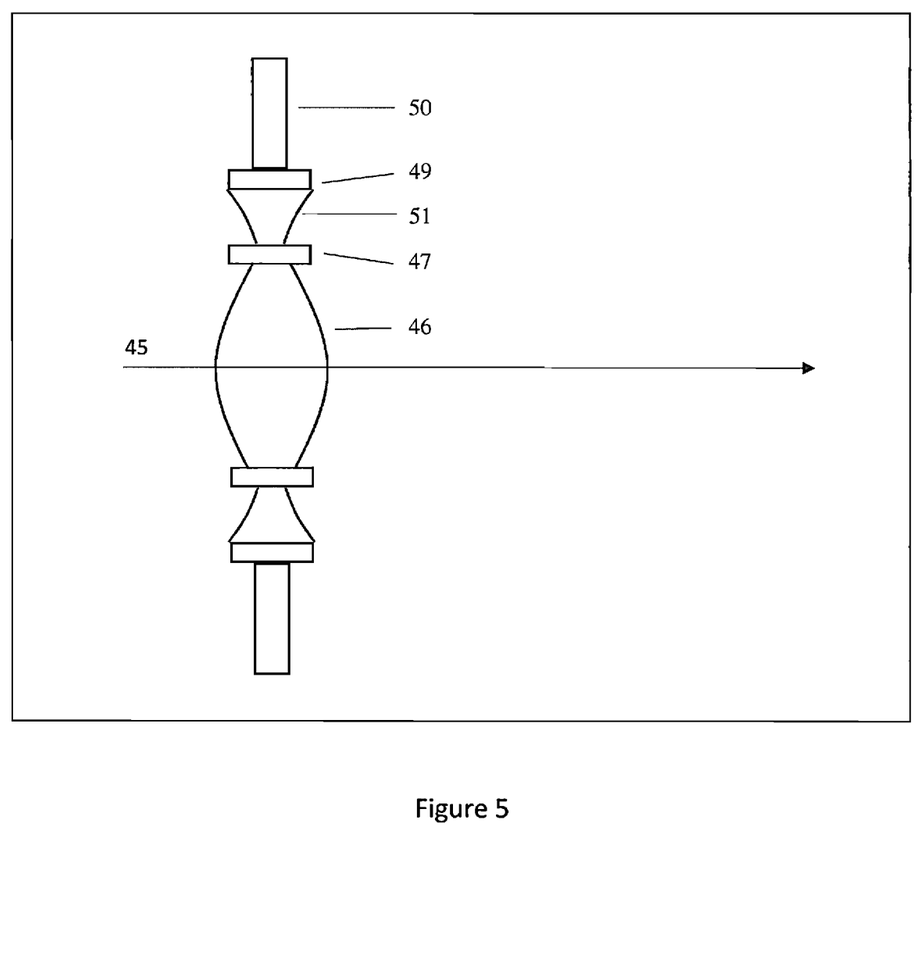
FIG. 5 illustrates the virtual aperture as a negative lens section.
Figure 6:
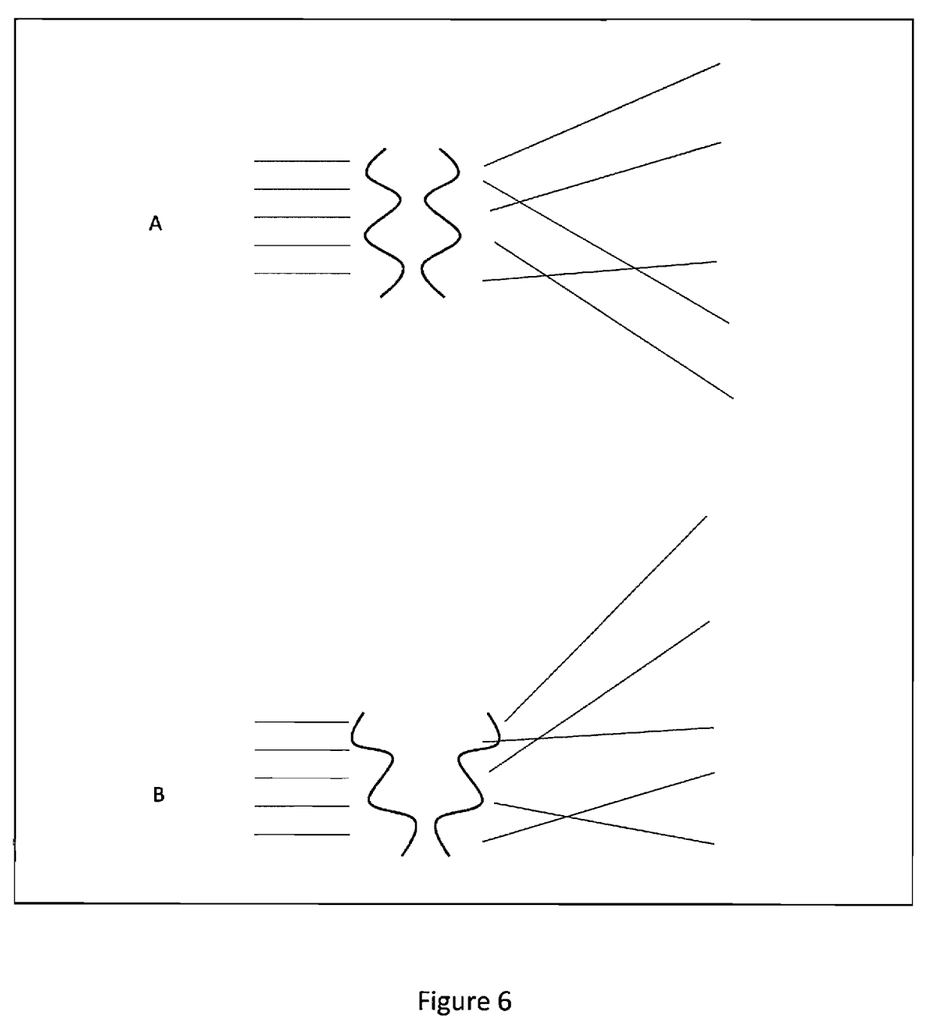

FIG. 5 illustrates another profile for the virtual aperture zone 51, namely a diverging lens profile. Note that this requires a thicker edge profile than the approach in FIG. 4. In FIG. 6A we show a close up of the preferred high-powered alternating positive and negative lens profiles with the incident and transmitted rays. FIG. 6B illustrates the effect of combining the profile in 6A with either an underlying prism or negative lens. In this case not only are the emergent rays scattered widely, they are directed away from the eye's macula, or central vision section of the retina, again, at the cost of a wider lens edge.

Figure 7:
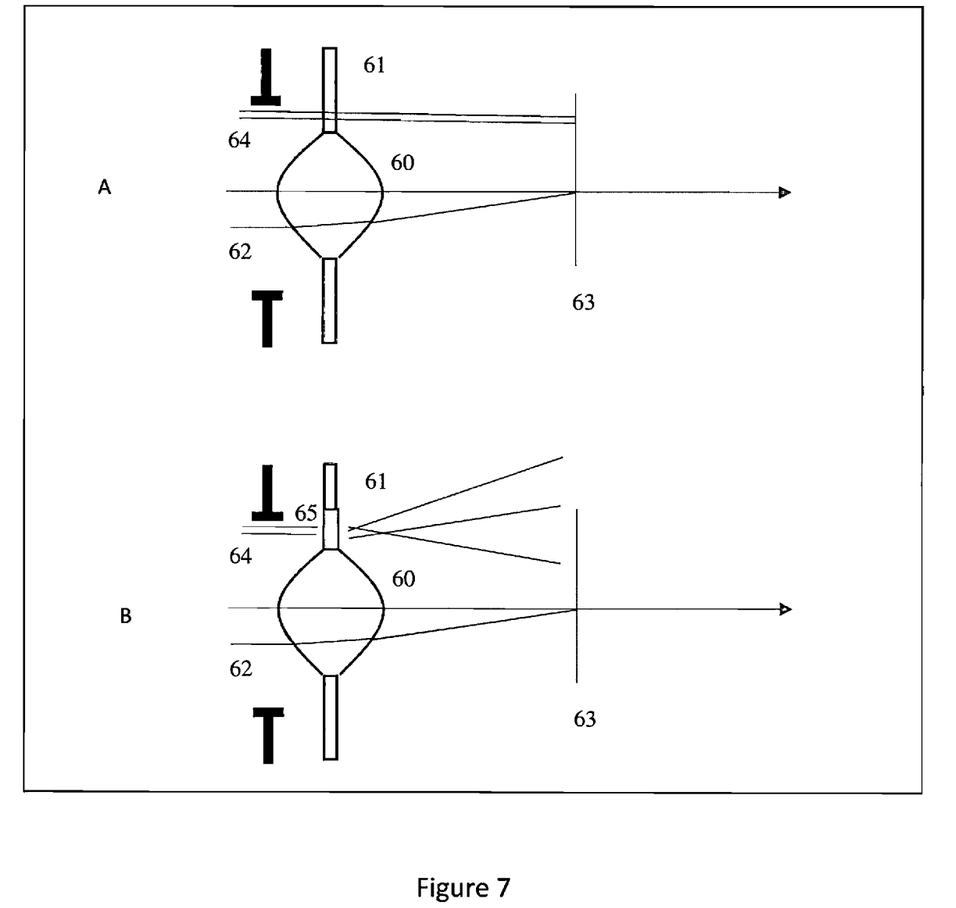

FIG. 7A illustrates a high-power IOL 60, usually with a relatively small optical diameter and large central thickness. When the eye's pupil is larger than the optical zone, incident rays 64 can miss the optic entirely and only intersect the haptic 61 on their way to the retina 63. This situation would cause noticeable artifacts in the peripheral vision of the eye. Incident rays 62, which intersect the optic zone as expected, are correctly refracted to the central vision of the retina. In FIG. 7B we illustrate the same optic, but now with a virtual aperture 65 between the optic and the haptic.

In this case, incident rays 64 which intersect the lens outside of the optical zone, are dispersed across the retina causing no apparent artifacts.

Taken together, these characteristics of an IOL which incorporates the virtual aperture can accurately be described as high definition (HD) and extended depth of field (EDOF).

The basic layout of the virtual aperture IOL is illustrated in FIG. 4. In the preferred embodiment, the diameter of the central optical zone 46 is 3.0 mm and the width of the virtual aperture 48 is 1.5 mm. Thus, the combination of central optical zone and virtual aperture is a 6.0-mm diameter optic, which is similar to common commercially available IOLs.

Spherical, Toric and zero aberrations optic zone. A significant portion of cataract patients have astigmatism in their cornea. After removal of the crystalline lens, the remaining optical system of the astigmatic cornea eye is ideally corrected with a toric, or astigmatic lens. For these patients, the central optical portion of our lens is made toric to provide improved visual correction. In addition, even though the optical portion is small, there is still some amount of spherical aberrations that could be corrected. Thus, the optimally corrected optical zone would provide spherical aberration correction for all lenses and toric correction for those patients who have corneal astigmatism.

The toric correction is easily made by those skilled in the art by providing two principle powers at two principle directions which would be aligned with the eye's corneal astigmatic powers.

The spherical aberrations for either the spherical or toric lens are corrected by employing a conic profile on one or more surfaces of the lens. Such a lens is said to have zero aberrations as there are zero monochromatic aberrations in the lens for an on-axis, distant object. The apical radius Ra of the conic profile is computed as usual for the desired paraxial power of the lens. A conic constant K is then selected based upon the lens material index of refraction, the lens center thickness, and the shapes of the front and back surface of the lens.

In the case where the correction is to be astigmatic, at least one of the lens surface shapes is biconic, having a conic profile in two orthogonal principal directions. In the preferred embodiment, the toric optic has an equal biconvex surface design where each surface is biconic. The non-toric optic has an equal biconvex surface design where each surface is conic. In both the biconic or conic surface case, the optimal conic constant K for the surfaces is determined using optical ray tracing known to those skilled in the art.

Multiple focal points. Some patients may prefer a multi-focal point optic providing vision correction for specific distances. One example is a bifocal optic which generally provides focusing power for both near and distant vision. Another example is a trifocal optic which provides focusing power for near, intermediate, and distant vision. In either case, to implement the multi-focal points IOL, the optical zone is modified to yield these focal zones using refractive or diffractive optical regions and the virtual aperture remains outside the last focal zone.

Figure 8:
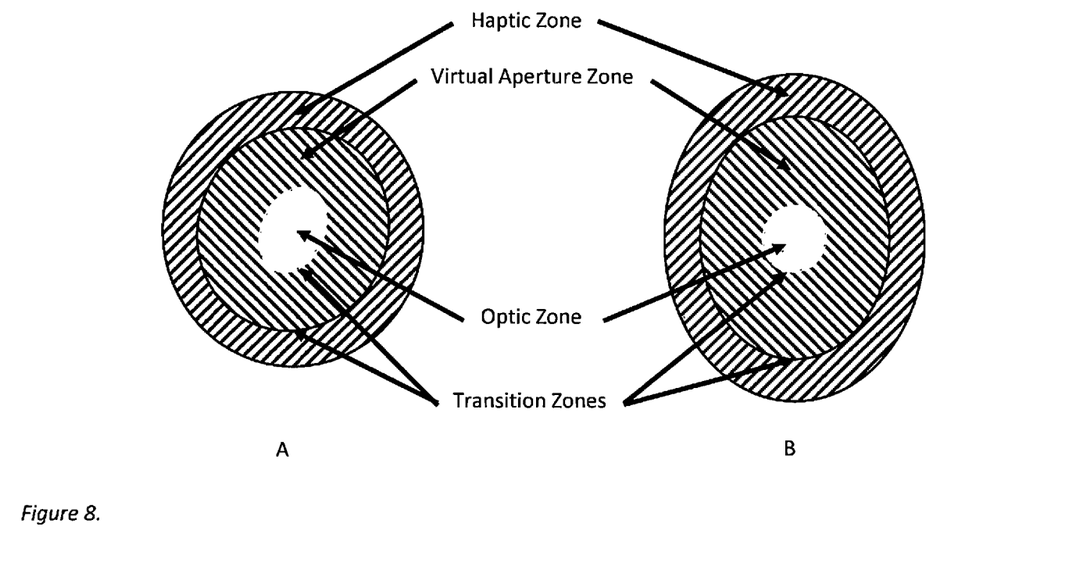
FIG. 8 illustrates lens A example of an oblong shaped optical zone and lens B example of a circular shaped optical zone.

In some applications, the virtual aperture can appear as an annular region with optical zones on each side of the annular region. The shape of the annular virtual aperture can also be free form, for example to accommodate an astigmatic optical zone or non-symmetric haptic region. This is illustrated in FIG. 8. In this Figure, lens A indicates an oblong shaped optical zone and so the inner contour of the virtual aperture must adapt to the shape. The inner haptic zone contour is circular, so the outer virtual aperture contour is circular. In this Figure, lens B depicts the optical zone as circular, so the virtual aperture inner contour is circular. The inner haptic contour is oblong, so the outer virtual aperture contour is oblong. In each case there are transition zones between each of the zones to smoothly connect the regions so that no visual artifacts are introduced into the eye. Alternatively, the transition regions can be of variable width so that the inner and outer virtual aperture contours can be any desired shape.

The IOL designs contemplated here can be made of any biocompatible optical material normally used for IOLs including hard and soft materials. They also can be manufactured using CNC machines or molds or other methods used to manufacture IOLs. The virtual aperture can be implemented as a one-dimensional profile that is symmetric in the azimuthal direction or a two-dimensional profile that implements tiny lens regions.

Figure 9:
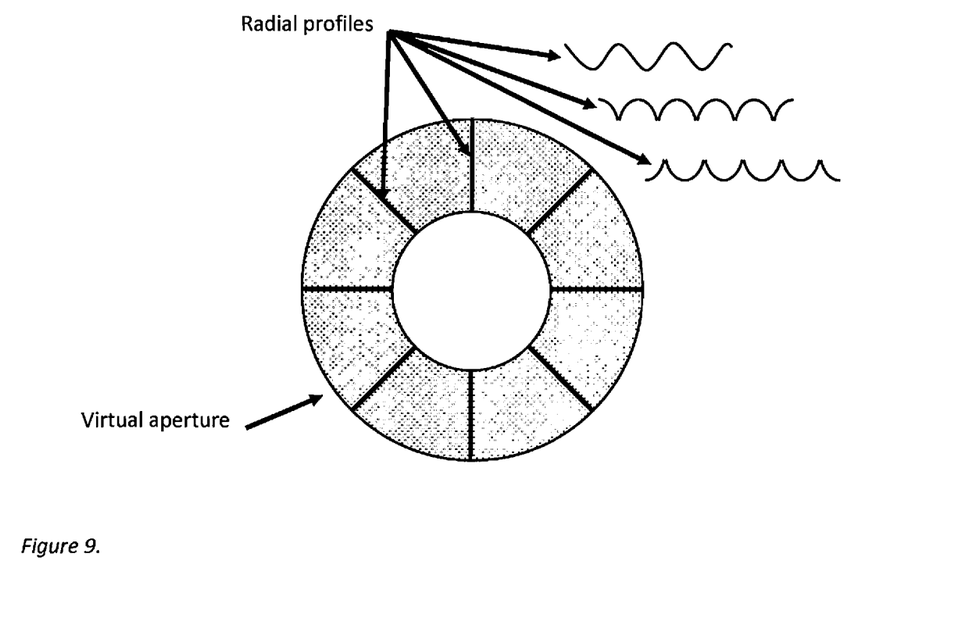
FIG. 9 illustrates azimuthally symmetric radial profiles.

In FIG. 9, illustrated is azimuthally symmetric radial profiles. The profiles can be all the same or adjusted in the azimuth direction. These profiles can be refractive or diffractive in nature. Although, eight distinct radial profiles are illustrated, the radial profiles are continuous in the azimuth direction. The radial profiles can have alternating positive and negative power, all positive power, or all negative power sections. The connections between all the power regions are smooth to prevent visual artifacts.

Figure 10:
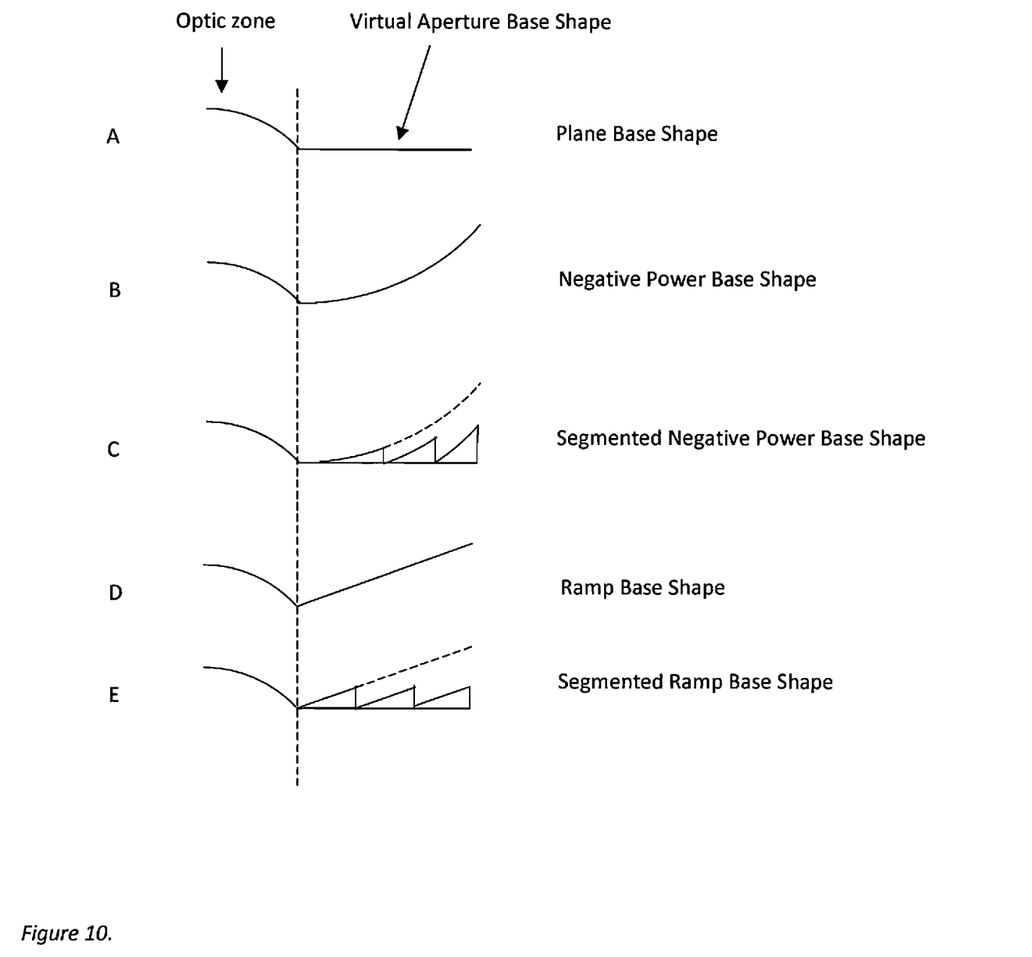
FIG. 10 illustrates symmetric radial profiles comparing elements A, B, C, D, & E.

In FIG. 10, illustrated are other symmetric radial profiles include combinations of planar, negative power, and ramp base shapes in addition to or instead of the high-power curves indicated in FIG. 8. Referring to FIG. 10, element A depicts a simple plane base shape. In FIG. 10, element B depicts a negative power base shape. This generally negative power curved profile can be represented by a portion of a sphere, a conic, or higher order curve such as a polynomial. FIG. 10, element C depicts a segmented negative power profile of element B, where the curve has been segmented similar to a Fresnel lens, to keep the overall lens thickness small. FIG. 10, element D depicts a ramp base shape profile and FIG. 10, element E depicts a segmented version of the ramp base shape, where the ramp has been segmented similar to a Fresnel lens, to keep the overall lens thickness small. Although the segmented profiles of elements C and E are illustrated with sharp discontinuities, in practice, the boundaries of the segments are implemented using smooth functions such as filets or Bezier curves to prevent observable artifacts caused by the sharp discontinuities. Additionally, a smooth transition region is placed between the optic zone and the virtual aperture as described elsewhere in this document. These base shapes can be used in conjunction with or instead of the high-power features to improve the effectiveness of the virtual aperture.

Figure 11:
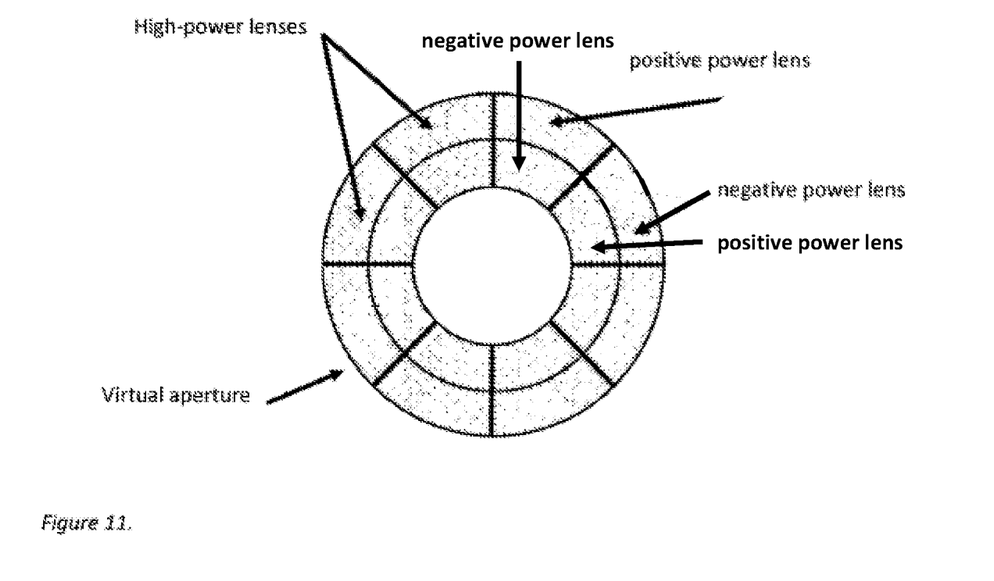
FIG. 11 illustrates two-dimensional lens regions.

FIG. 11 illustrates two-dimensional lens regions oriented in a polar sampling. The high-power lenses alternate in positive and negative power in both the radial and azimuthal directions. Two positive power lenses and two negative power lenses are illustrated in the figure. The actual geometry of these two-dimensional polar lenses is on the order of the radial profiles.

Alternatively, the two-dimensional high-power lenses could be all positive or all negative lenses. In this case, the high-power lenses are separated by small smooth transition regions (for example, a continuous polynomial interpolator such as a Bezier curve) to prevent visual artifacts. This is the preferred two-dimensional high-power lens structure when there is more than one lens sample rate in the azimuth direction. In this case, the individual lenses look like small pillows where the pillows are above the base surface for positive power lenses and are below the surface for negative power lenses.

Figure 12:
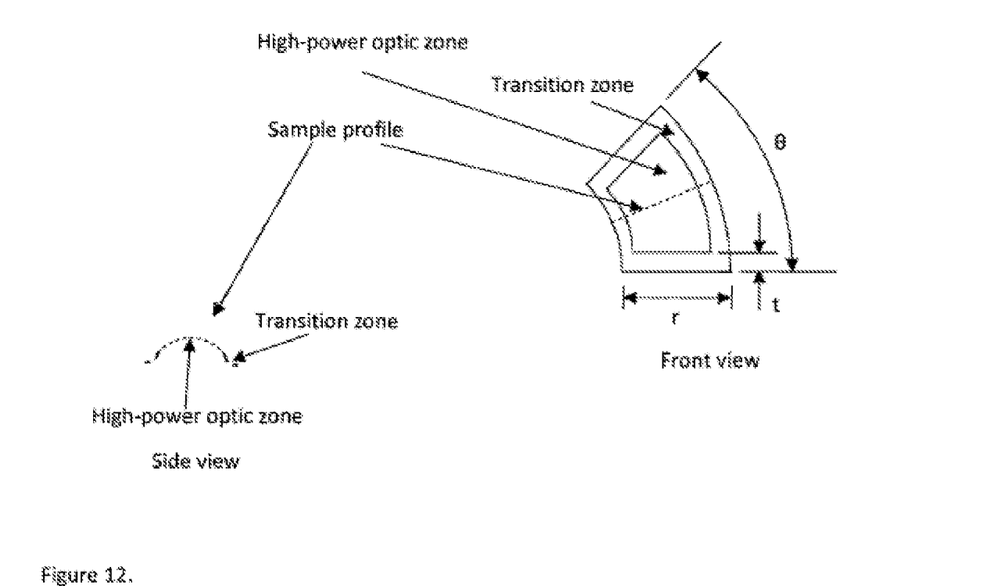
FIG. 12 illustrates the geometry for one of the two-dimensional high-power lenses.

FIG. 12 illustrates the geometry for one of the two-dimensional high-power lenses. In the upper right portion of the figure we show a front view of the high-power lens. There is a central high-power optical region and a surrounding transition region. The radial extent of this region is given by r, the width of the transition region is given by t, and the azimuthal subtense is given by theta. In the lower left portion of the figure we show a side view of one of the profiles of the lens. The central part represents the high-power optical zone and the two side curves represent the transition zones. The interface between the optical zone and the transition zones has zero- and first-order continuity. At the edge of the lens boundary, the transition is coincident with the virtual aperture base shape (which is typically a vertical line on the IOL). At the edge of the lens there is also zero- and first-order continuity between the transition curve (typically a polynomial curve) and the edge. The shape of this small high-power lens region is set so that the radial extent r is approximately equal to the arc-length of the center portion of the region.

The central optical zone can be designed using standard IOL design concepts to provide sphere, cylinder, and axis correction, as well as higher-order correction such as spherical aberration control. These design concepts are known to those skilled in the art.

The preferred virtual aperture profiles illustrated in FIG. 4 have alternating positive and negative lens profiles with focal lengths on the order of +/−1.5 mm. These lens surface profiles can be generated using conics, polynomials (such as cubic Bezier splines), rational splines, and combinations of these and other curves. The geometry of the lens profiles is selected to adequately disperse the transmitted optical rays across the retina and at the same time be relatively easy to manufacture on a high-precision lathe or with a mold process. It is also possible to place a smooth surface on one profile (for example the front surface) and the small high-power lens profiles on the other surface profile (for example the back surface).

Using the preferred virtual aperture profiles illustrated in FIG. 4, the edge thickness of the IOL and the center thickness of the central optical zone can be quite small, even for high-power IOLs. The material of the lens is the same as those used for other soft or hard IOL designs.

The IOL design provides very good, high-definition, distance vision and the range of "clear vision" can be controlled by specification of what is meant by "clear vision" (e.g., 20/40 acuity), and the relative size of the central optic zone and the virtual aperture width. A simple equation [Smith G, Relation between spherical refractive error and visual acuity, Optometry Vis. Sci. 68, 591-8, 1991] for estimating the acuity given the pupil diameter and spherical refractive error is given in equation (1a and 1b).

$$A = kDE \qquad (1a)$$

$$A = \sqrt{1+(kDE)^2} \qquad (1b)$$

A=acuity in minutes of arc (A=Sd/20), that is, the minimum angle of resolution
k=a constant determined from clinical studies, mean value of 0.65
D=pupil diameter in mm
E=spherical refractive error in diopters
Sd=Snellen denominator The second equation is postulated as being more accurate for low levels of refractive error, and gives a reasonable result.

For E=0, A=1 min of arc or 20/20.
Solving (1b) for E yields equation (2).

$$E = \frac{\sqrt{A^2 - 1}}{kD} \qquad (2)$$

Equation (1b) tells us the acuity A given the range of depth of field (E×2) in diopters and the pupil diameter D.
Equation (2) tells the range of depth of field in diopters given the acuity A and the pupil diameter D. For example, for:
Acuity of 20/40, A=40/20=2 min arc
D=3.0 mm
k=0.65

$$E = \frac{\sqrt{2-1}}{0.65 \times 3.0} = 0.89$$

Depth of field=2E=1.8 D. Using (1b), $$A = \sqrt{1+(0.65 \times 3.0 \times 0.89)^2} = 2$$

The concept of the virtual aperture can be employed in phakic or aphakic IOLs, a corneal implant, a contact lens, or used in a cornea laser surgery (LASIK, PRK, etc.) procedure to provide an extended depth of field and/or to provide high-definition vision. Also, it would be possible to replace the virtual aperture with an actual opaque aperture and realize the same optical benefits as the virtual aperture.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An intraocular lens for providing improved vision on an individual's retina, said intraocular lens comprising:
a virtual aperture positioned in a first periphery region of said intraocular lens and connected to an optical zone by a first transition region;
a haptic positioned in a second periphery region and connected to said virtual aperture by a second transition region, said second periphery region radially further peripherally from said optical zone than said first periphery region;
wherein said first transition region comprises a zero-order and first-order continuity; and
wherein either said virtual aperture comprises high-power positive and high-power negative lens profiles wherein light rays intersecting said virtual aperture are widely distributed across the retina to reduce monochromatic and chromatic aberrations and defocus due to a change in focal length thereby enhancing the individual's depth of field;
or said virtual aperture comprises one or more prism profiles in conjunction with alternating high-power positive and high-power negative lens profiles selected from the group consisting of sequential conics, polynomials, rational splines, and diffractive profiles wherein light rays intersecting said virtual aperture are widely distributed across the retina to reduce monochromatic and chromatic aberrations and defocus due to a change in focal length thereby enhancing the individual's depth of field.

2. The intraocular lens according to claim 1, wherein said high-power positive and high-power negative lens profiles are smooth.

3. The intraocular lens according to claim 1, wherein a posterior side of said haptic includes a square edge to inhibit cell growth.

4. The intraocular lens according to claim 1 wherein said virtual aperture provides a contrast for resolution of an image over a selected range of distances.

5. The intraocular lens according to claim 1, wherein said high-power positive and high-power negative lens profiles are arranged in a sequence.

6. The intraocular lens according to claim 1, wherein said high-power positive and high-power negative lens profiles are alternating.

* * * * *